United States Patent
Ichikawa et al.

(10) Patent No.: US 9,463,243 B2
(45) Date of Patent: Oct. 11, 2016

(54) AMORPHOUS MEDICINAL FINE PARTICLES PRODUCED BY PULSED LASER ABLATION IN LIQUID AND THE PRODUCTION METHOD THEREOF

(71) Applicants: Yuki Ichikawa, Ann Arbor, MI (US); Andrius Marcinkevicus, Saline, MI (US)

(72) Inventors: Yuki Ichikawa, Ann Arbor, MI (US); Andrius Marcinkevicus, Saline, MI (US)

(73) Assignee: IMRA AMERICA, INC., Ann Arbor, MI (US)

(*) Notice: Subject to any disclaimer, the term of this patent is extended or adjusted under 35 U.S.C. 154(b) by 88 days.

(21) Appl. No.: 13/765,769

(22) Filed: Feb. 13, 2013

(65) Prior Publication Data
US 2013/0209523 A1  Aug. 15, 2013

Related U.S. Application Data

(60) Provisional application No. 61/598,002, filed on Feb. 13, 2012.

(51) Int. Cl.
| | |
|---|---|
| *A61K 9/00* | (2006.01) |
| *A61K 41/00* | (2006.01) |
| *A61J 3/02* | (2006.01) |
| *A61K 9/50* | (2006.01) |
| *A61K 9/51* | (2006.01) |

(52) U.S. Cl.
CPC .................. *A61K 41/00* (2013.01); *A61J 3/02* (2013.01); *A61K 9/50* (2013.01); *A61K 9/51* (2013.01); *Y10T 428/2982* (2015.01)

(58) Field of Classification Search
USPC ........................................................ 424/400
See application file for complete search history.

(56) References Cited

U.S. PATENT DOCUMENTS

| 7,597,278 B2 | 10/2009 | Asahi |
|---|---|---|
| 2009/0246530 A1 | 10/2009 | Murakami et al. |

(Continued)

FOREIGN PATENT DOCUMENTS

| EP | 2033616 A1 | 3/2009 |
|---|---|---|
| JP | 2005238342 A | 9/2005 |

OTHER PUBLICATIONS

Yamada (Chem. Pharm. Bull. 47(9) 1311-1313 (1999)).*
Liu (J Pharm Pharmaceut Sci 13(4) 589-606, 2010).*

(Continued)

*Primary Examiner* — Devang Thakor
(74) *Attorney, Agent, or Firm* — Dickinson Wright PLLC

(57) ABSTRACT

The present disclosure is directed to an in-liquid laser-based method for fabricating a solution of fine particles of amorphous solid medicinal compounds, a solution of fine particles of amorphous medicinal agents made with the method, and fine particles made with the method. By using a target solidified via a phase transition process to covert an initial crystalline structure into an amorphous solid, technical difficulties with handling a hydraulically-pressed target are overcome. The laser-based ablation process produces amorphous solid medicinal compound fine particles, which improves the bioavailability and solubility of the medicinal compound. The improvement results from a combination of: disordered crystalline structure and enlarged relative surface area by particle size reduction. The laser based method may be carried out with ultrashort pulsed laser systems, or with UV nanosecond lasers. Results obtained with an ultrashort near IR laser and a UV nanosecond laser show formation of amorphous solid curcumin fine particles.

23 Claims, 9 Drawing Sheets

(56) References Cited

U.S. PATENT DOCUMENTS

2010/0196192 A1    8/2010    Liu et al.
2011/0196044 A1    8/2011    Hu et al.

OTHER PUBLICATIONS

Takebe (International Journal of Pharmaceutics 414 (2011) 244-250; May 7, 2011).*
International Search Report for PCT/US2013/025845; 2 Pages Dated May 10, 2013.
P. Anand et al., "Bioavailability of Curcumin: Problems and Promises", Molecular Pharmaceutics, vol. 4, No. 6 (2007) 807.
Barcikowski et al., "Generation of nanoparticles colloids by picosecond and femtosecond laser ablation in liquid flow", Applied Physics Letters, vol. 91 (2007) 083113.
R. Benassi et al.,"Theoretical study on Curcumin: A comparison of calculated spectroscopic properties with NMR, UV-vis and IR experimental data", Journal of Molecular Structure, 892 (2008) 168.
J. Breitenbach et al., "Melt extrusion: from process to drug delivery technology", European Journal of Pharmaceutics and Biopharmaceutics, vol. 54, 107 (2002).
K. J. Crowley et al., "The use of thermal methods for predicting glass-former fragility", Thermochimica Acta, vol. 380, 79 (2001)).
Z. Dong et al., "Evaluation of solid state properties of solid dispersions prepared by hot-melt extrusion and solvent co-precipitation", International Journal of Pharmaceutics, vol. 355, 141 (2008).
Y. Kawabata et al., "Formulation design for poorly water-soluble drugs based on biopharmaceutics classification system: Basic approaches and practical applications", International Journal of Pharmaceutics, vol. 420, 1-10, (2011).
Kenth et al., "Fabrication of Paclitaxel Nanocrystals by Femtosecond Laser Ablation and Fragmentation", Journal of Pharmaceutical Science, vol. 100, No. 3 (2011) 1022.
M. Murakami et al., "Burst-Mode Femtosecond Pulsed Laser Deposition for Control of Thin Film Morphology and Material Ablation", Applied Physics Express, vol. 2, 042501 (2009).
S. Nafisi et al., "Curcumin Binding to DNA and RNA", DNA and Cell Biology vol. 28 No. 4(2009) 201.
G. G. Osborn et al., "Current Treatments for Patients With Alzheimer Disease", The Journal of the American Osteopathic Association, Sep. 1, 2010 vol. 110 No. 9 suppl. 8 S16-S26.
J. Park et al., "Preparation and pharmaceutical characterization of amorphous cefdinir using spray-drying and SAS-process", International Journal of Pharmaceutics, vol. 396, 239 (2010).
T. L. Rogers et al., "Enhanced Aqueous Dissolution of a Poorly Water Soluble Drug by Novel Particle Engineering Technology: Spray-Freezing into Liquid with Atmospheric Freeze-Drying", Pharmaceutical Research, vol. 20, 485 (2003).
R. A. Sharma et al., "Curcumin: The story so far", European Journal of Cancer vol. 41 (2005) 1955.
J. P. Sylvestre et al., "Nanonization of megestrol acetate by laser fragmentation in aqueous miliu", Journal of Controlled Release vol. 149, 273 (2011).
D. L. Teagarden et al., "Practical aspects of lyophilization using non-aqueous co-solvent systems", European Journal of Pharmaceutical Sciences, vol. 15, 115 (2002).
J. Yao et al., "Characterization of electrospraying process for polymeric particle fabrication", Aerosol Science, vol. 39, 987 (2008).
L. Yu et al., "Amorphous pharmaceutical solids: preparation, characterization and stabilization", by Advanced Drug Delivery Reviews, vol. 48, 27 (2001).

* cited by examiner

AMORPHOUS MEDICINAL FINE PARTICLES PRODUCED BY PULSED LASER ABLATION IN LIQUID AND THE PRODUCTION METHOD THEREOF

RELATED APPLICATIONS

This application claims the benefit of U.S. provisional application Ser. No. 61/598,002 filed Feb. 13, 2012.

TECHNICAL FIELD

The present invention is relates to laser-based methods and systems for forming amorphous medicinal fine particles, and a solution produced therewith.

BACKGROUND

Improving the bioavailability of poorly water-soluble medicinal compounds has been an on-going challenge and remains of particular interest to many pharmaceutical researchers and pharmaceutical companies. In the present specification and claims a medicinal compound refers to a compound or formulation used to treat a medical condition and to a compound or formulation used as a precursor to create another medicinal compound.

An amorphous solid is characterized as a solid that does not have long-range order in its structure like a crystalline solid; it may have some short-range order on an atomic length scale because of chemical bonding. An amorphous solid has a disordered structure rather than a crystalline structure. Experimentally, the amorphicity of a solid can be characterized by an x-ray diffraction (XRD) pattern wherein no Bragg peaks are observed. To avoid any ambiguity in the present specification and claims, an amorphous solid is defined as a solid that does not exhibit Bragg peaks in its x-ray diffraction pattern when the x-ray exposure and detection parameters are sufficient to detect the Bragg peaks in a similar amount of the crystalline solid.

Because of its disordered structure, the enthalpy of an amorphous solid is higher than in a crystalline solid. The molecules are in an unstable energy state in the amorphous solid. This frustrated crystalline form causes an amorphous solid to have higher solubility than a crystalline solid does. According to a review paper, see Y. Kawabata et al.: International Journal of Pharmaceutics, Vol. 420, 1, (2011), the solubility difference between an amorphous solid and crystalline solid is typically from 1.1 to 1000 fold. Thus, use of an amorphous solid form of a medicinal compound is known as a way to improve its bioavailability because of the enhanced solubility due to its particular physical form.

Another strategy to improve bioavailability of a medicinal compound is to enlarge the relative surface area compared to the particle size by reducing the particle size of a drug using such as by a wet grinding process, a high pressure homogenization process, or a fluid bed spray-drying process. However, these methods have significant limitations. As exemplified in U.S. Pat. No. 7,597,278, in-liquid laser pulverization is an emerging technology to produce fine sized particles of medicinal compounds. A laser based approach offers many advantages over the conventional methods such as wet grinding, high pressure homogenization, or fluid bed spray-drying. A desirable advancement in such laser based processes would be to improve bioavailability, enhance solubility, and increase the yield of the particles.

SUMMARY OF THE INVENTION

In one aspect, the present invention provides a suspension of amorphous fine particles of a medicinal compound using in-liquid laser ablation. The present invention finds special use with medicinal compounds that are poorly water soluble when in a crystalline solid form. Various embodiments improve bioavailability and solubility of a medicinal compound due to the combination of at least two features: a disordered amorphous structure and an enlarged relative surface area by particle size reduction.

In one aspect, a bulk medicinal compound prepared as a target for in-liquid laser ablation was transformed through at least one phase transition to modify its physical form from a crystalline solid to an amorphous solid prior to ablation.

In one aspect, amorphous fine particles of a medicinal compound produced with various embodiments have a complex ultrafine structure in the scale of 200 nanometers (nm) or smaller, which permits an increased relative surface area for each particle.

In one aspect, the disordered amorphous structure of the fine particles produced by the present invention has a distinctive x-ray diffraction pattern compared to the crystalline fine particles, the amorphous solids according to the present invention do not display Braggs peaks in the x-ray diffraction pattern. Vibrational spectroscopy may also be used to confirm that the molecular structure of the solid bulk material target is sustained through the laser ablation process.

The amorphous fine particles formed according to the present invention can be extracted from the ablation/suspension liquid or kept in the ablation liquid as a colloidal suspension.

In another aspect, a phase transition process such as melting is involved in the target preparation. The phase transition not only modifies the crystalline structure to produce an amorphous solid target material but it also mitigates problems of conventional laser ablation wherein the target is made from a hydraulically-pressed powder.

DETAILED DESCRIPTION

As used herein "laser fragmentation" refers to a laser pulverization process wherein a suspension of particles is irradiated with a laser, for example as disclosed in U.S. Pat. No. 7,597,278.

As used herein "laser ablation" refers to a laser pulverization process where a bulk target material is irradiated with a laser, for example as disclosed in "Fabrication of Paclitaxel Nanocrystals by Femtosecond Laser Ablation and Fragmentation" by Kenth et al. Journal of Pharmaceutical Science, Vol. 100, No. 3 (2011) 1022, and in U.S. patent application Ser. No. 12/951,496 filed Nov. 22, 2010 entitled "Production of Organic Compound Nanoparticles With High Repetition Rate Ultrafast Pulsed Laser Ablation In Liquids".

In at least one embodiment the present invention comprises a pulsed laser-based method for production of amorphous fine particle medicinal compounds. The amorphous state is advantageous for improving the bioavailability of poorly water-soluble medicinal compounds. In the present specification and claims the term poorly water soluble medicinal compound refers to a medicinal compound having a water solubility of 10 grams/liter or less, more preferably 1 grams/liter or less and most preferably 100 milligrams/liter or less Furthermore, various limitations of prior in-liquid laser ablations or laser fragmentation are overcome by modifying the physical state of the bulk target through a phase transition process.

Figure 1C:
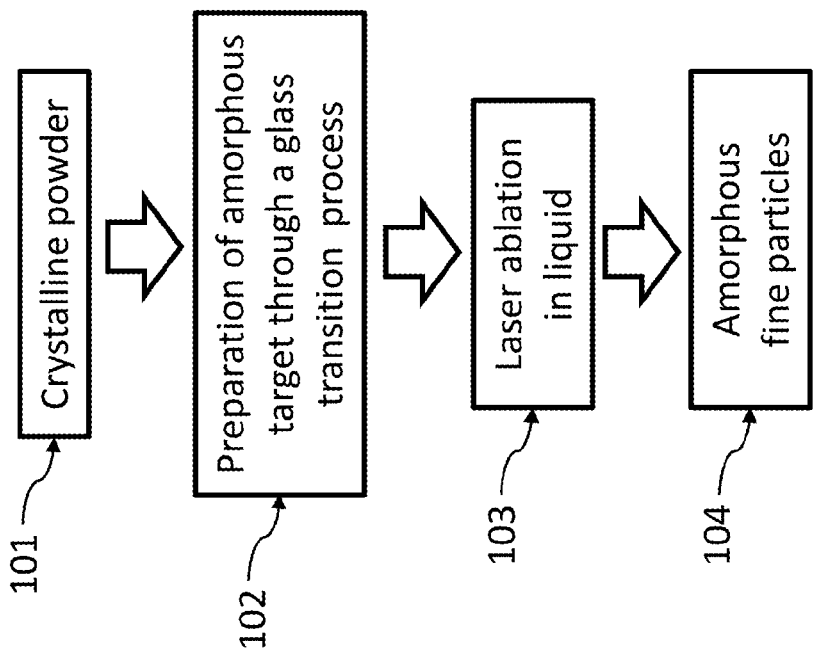
FIG. 1c is a block diagram illustrating a method of laser ablation according to the present invention.
Figure 1B:
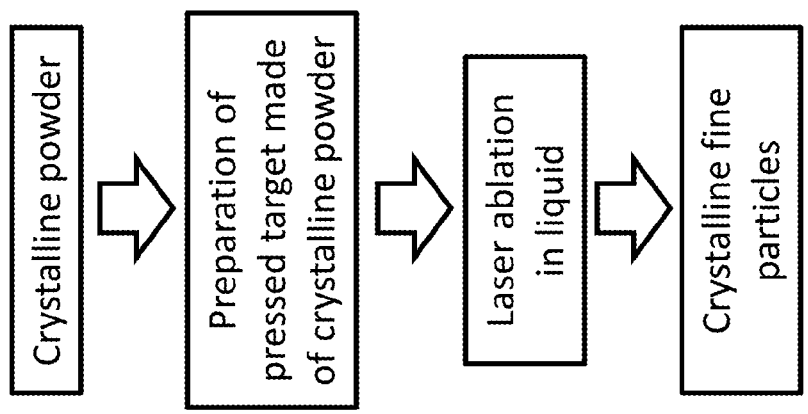
FIG. 1b is a block diagram illustrating a prior art method of laser ablation.
Figure 1A:
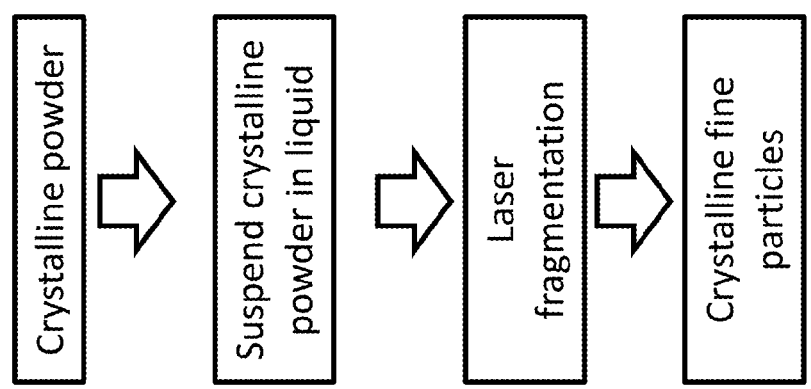
FIG. 1a is a block diagram illustrating a prior art method of laser fragmentation.

FIGS. 1a-1c illustrate three in-liquid laser pulverization processes. FIG. 1a is a block diagram illustrating a prior art method of laser fragmentation as generally described in U.S. Pat. No. 7,597,278 (the '278 patent). The '278 patent discloses a method of producing a suspension of medicinal nanoparticles based on a laser pulverization process we refer to as laser fragmentation. The process includes at least the two steps of: 1) forming an initial suspension of medicinal compound particles; and 2) irradiating the suspension with a laser. Although a mean particle size of about 100 nanometers (nm) was obtained and the resulting nanoparticle suspension was deemed useful for a drug delivery system, this laser based method has some limitations. First, the efficiency of the laser fragmentation process is driven by the probability that a suspended particle will enter the laser focal volume where the laser pulverization can take place. It follows from this that some population of particles will remain untreated and some population of particles can be overexposed to laser irradiation, which causes unwanted decomposition of the medicinal compound. Second, because the laser beam becomes more scattered with an increase in the number of particles in the suspension as the process proceeds it becomes even less efficient.

FIG. 1b is a block diagram illustrating a second prior art method based on laser ablation as generally disclosed in "Fabrication of Paclitaxel Nanocrystals by Femtosecond Laser Ablation and Fragmentation" by Kenth et al. Journal of Pharmaceutical Science, Vol. 100, No. 3 (2011) 1022, (Kenth et al.). This method utilizes a different configuration for the laser pulverization process which we refer to as laser ablation, so as to distinguish it from processing of a suspension of particles in a laser fragmentation process as described above. In the method of Kenth et al., a tablet of hydraulically pressed crystalline paclitaxel powder was utilized. Applicants expect that the pressed powder configuration reduces the inefficiency of the laser based process of FIG. 1a. A pressed tablet has a flat surface on which consistent laser ablation can occur as long as the focus position of laser is within a suitable range. However, in the process of Kenth et al. after laser ablation without any further processing steps the particle size distribution remained about 3 micrometer as shown in Table 2 of the paper, which is relatively large. Without subscribing to any particular theory, Applicants believe one reason is that in the process of Kenth et al. a laser pulse pulverizes not only the tablet surface but also disintegrates the pressed tablet back into the powder particles due to the laser-produced acousto-mechanical impact. This effect of the laser interaction may result in a large amount of untreated particles in the suspension. Notably, Applicants have found that a tablet of pressed powder is sometimes so fragile that it can be broken, thereby destroying the surface flatness for the laser ablation process, when it is taken out of the hydraulic press container. Furthermore, even after succeeding in successfully removing the tablet, it can be difficult to handle. Such a pressed tablet becomes looser when submerged in a liquid, especially in a liquid that is flowing. On the other hand, such liquid flow, among other things, greatly improves the pulverization efficiency of the laser ablation process. For example, see "Generation of nanoparticles colloids by picosecond and femtosecond laser ablation in liquid flow" by Barcikowski et al.; Applied Physics Letters, Vol. 91 (2007) 083113 and U.S. patent application Ser. No. 12/320,617, filed Jan. 30, 2009, which is incorporated by reference in its entirety, entitled "Production of Metal and Metal-Alloy Nanoparticles With High Repetition Rate Ultrafast Pulsed Laser Ablation In Liquids". In addition, a tablet of pressed crystalline powder is not the best form to be laser-pulverized because the fine particles produced with laser ablation will retain the crystalline structure of the starting powder. For example, U.S. patent application Ser. No. 12/951,496, referenced above, discloses an ultrashort laser based process in which the resultant crystalline fine particles are formed. As discussed above, an amorphous structure is preferred for bioavailability of medicinal compounds.

FIG. 1c is a block diagram illustrating a method of laser ablation according to the present invention. Hereinafter we disclose a method of laser ablation to create amorphous medicinal compound fine particles. Instead of pressing a crystalline powder into a target form, transformation of the crystalline powder into a solidified amorphous form allowed us to solve the conventional technical problems with handling a hydraulically-pressed crystalline target material. Simultaneously, amorphous fine particles of the medicinal compound are created which, based on our experiments, surprisingly resulted from the process disclosed herein. Thus, two advantageous features are combined i.e. disordered amorphous structure and enlarged surface area caused by particle size reduction. As with the prior processes a crystalline medicinal compound power is the initial starting material (101). In the present invention an initial step is the formation of an amorphous medicinal compound material (102) prior to laser ablation, and will be discussed below.

Figure 2:
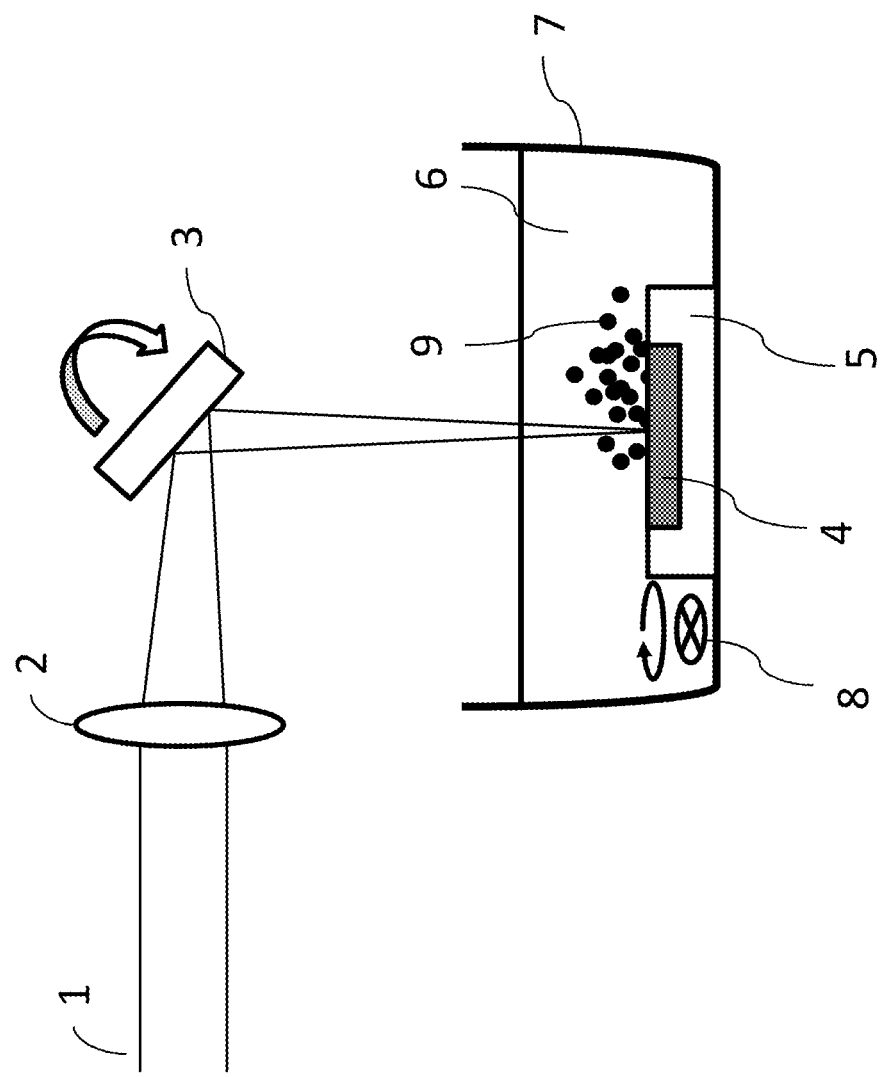
FIG. 2 schematically illustrates a portion of a laser based system for producing amorphous medicinal compound fine particles in a liquid according to the present invention.

Referring to the laser ablation step 103 of FIG. 1c, FIG. 2 schematically illustrates a portion of a laser based system for producing amorphous medicinal compound fine particles in a liquid according to the present invention. In one embodiment, a laser beam 1 is delivered by a pulsed laser source, not shown, focused by a lens 2, and guided by a guide mechanism 3, which also could be placed before lens 2, onto a target 4. The target 4 mounted in a target holder 5 is an amorphous, pellet shaped, solid containing the medicinal compound of interest. The target 4 and the target holder 5 are submerged by several millimeters and preferably less than 1 cm, below the surface of a liquid 6 in a container 7. The flow of the liquid 6 generated by the movement of a stirring bar 8 can help prevent the generated fine medicinal compound particles 9 from remaining in the laser irradiating area. The flow of liquid 6 also cools the laser focal volume.

The liquid layer thickness is determined by the negligible linear as well as nonlinear absorption of the laser beam 1. Thus the wavelength of the laser source can be from the mid-infrared to near-infrared range (e.g. about 2000 nanometers to 780 nanometers); in the visible range (e.g. 700 nanometers to 400 nanometers) or down to the ultraviolet range (e.g. 395 nanometers to 266 nanometers). The beam 1 preferably has a pulse energy of from 10 nanoJoule (nJ) to 2 milliJoule (mJ), more preferably from 50 nJ to 300 microJoules (µJ), and most preferably from 0.1 to 100 microJoules. The beam 1 may have a pulse duration from 10 femtoseconds (fs) to 100 nanoseconds (ns), preferably from 10 femtoseconds to 10 nanoseconds, and most preferably from 30 femtoseconds to 10 picoseconds (ps). Extremely short pulse durations, for example shorter than 100 femtoseconds reduce unwanted thermal effects, but when the pulse duration approaches several tens of femtoseconds or when the liquid layer has a non-negligible thickness, the temporal broadening of the pulse due to the wavelength dispersion of the refractive index in the liquid becomes significant. In that case, an additional optical component for dispersion compensation may be inserted in the optical path to compensate. The optical components for dispersion compensation include, but are not limited to, a pair of optical diffractive gratings and a pair of volume Bragg gratings. Also insertion of a material having a dispersion of the opposite sign to one encountered in the disclosed set-up or an optical waveguide including, but not limited to, an optical fiber, a photonic crystal fiber, a photonic band gap fiber, a non-linear optical fiber, and fiber Bragg grating can compensate the effect of pulse duration broadening. Preferably the beam 1 has a pulse repetition rate of from 1 kHz to 100 MHz, more preferably from 10 kHz to 1 MHz, and in some embodiments may be in the range from about 100 KHz to 1 MHz, and/or up to about 10 MHz. The guide mechanism 3 can be a vibration mirror 3 configured for fast scanning or other movement of the laser beam 1 on the surface of the target 4. The mirror 3 vibration frequency is preferably 10 Hz or greater with angular amplitude of 1 mrad or greater, such that a scanning speed on the surface is 0.01 meters per second or greater. Such a mirror can be a piezo-driven mirror, a galvanometer mirror, or other suitable apparatus for beam movement. Two or more mirrors can be used to achieve a two-dimensional movement in the image plane of the objective lens. Ideally, the image plane and the target surface are entirely in parallel, and more preferably the incident angle of the laser beam pulse on the target is a constant angle independent of the position of the spot in the image plane. Another lens or lens system can be also implemented to adjust the position of the focusing point along the optical path.

Referring to the amorphous target preparation step 102 of FIG. 1c, the target 4 can be a solid medicinal compound in an amorphous form prepared by melting and quenching a crystalline medicinal compound, which may be originally in an available powder form, for example, crystalline curcumin powder from SIGMA-ALDRICH as described below. The amorphous target 4 can be also made by several other known ways, a preferred method being melt-extrusion. See for example "Melt extrusion: from process to drug delivery technology" by J. Breitenbach: European Journal of Pharmaceutics and Biopharmaceutics, Vol. 54, 107 (2002) or "The use of thermal methods for predicting glass-former fragility" by K. J. Crowley et al.: Thermochimica Acta, Vol. 380, 79 (2001)). Other methods include but are not limited to: spray-drying, see "Preparation and pharmaceutical characterization of amorphous cefdinir using spray-drying and SAS-process" by J. Park et al.: International Journal of Pharmaceutics, Vol. 396, 239 (2010); spray freezing, see "Enhanced Aqueous Dissolution of a Poorly Water Soluble Drug by Novel Particle Engineering Technology: Spray-Freezing into Liquid with Atmospheric Freeze-Drying" by T. L. Rogers et al.: Pharmaceutical Research, Vol. 20, 485 (2003); lyophilization, see "Practical aspects of lyophilization using non-aqueous co-solvent systems" by D. L. Teagarden and D. S. Baker: European Journal of Pharmaceutical Sciences, Vol. 15, 115 (2002); electrospraying, see J. Yao et al.: Aerosol Science, Vol. 39, 987 (2008); solvent co-precipitation, see "Evaluation of solid state properties of solid dispersions prepared by hot-melt extrusion and solvent co-precipitation" by Z. Dong et al. International Journal of Pharmaceutics, Vol. 355, 141 (2008); dehydration of hydrated compounds, see "Amorphous pharmaceutical solids: preparation, characterization and stabilization" by L. Yu et al.: Advanced Drug Delivery Reviews, Vol. 48, 27 (2001); and supercritical anti-solvent process, see "Preparation and pharmaceutical characterization of amorphous cefdinir using spray-drying and SAS-process" by J. Park et al.: International Journal of Pharmaceutics, Vol. 396, 239 (2010) or see "Enhanced Aqueous Dissolution of a Poorly Water Soluble Drug by Novel Particle Engineering Technology: Spray-Freezing into Liquid with Atmospheric Freeze-Drying" by T. L. Rogers et al.: Pharmaceutical Research, Vol. 20, 485 (2003). Any of these processes might be used to convert the starting material, a crystalline solid, into an amorphous solid material as defined in the present specification through a phase transition process.

In order for the amorphous target 4 to have a flat surface, which is preferred for a laser ablation process, a molding step such as thermoforming or a shaping step such as a pressing, machining and postforming process can be applied to the amorphous solid. The target 4 may further contain an excipient to enhance the solubility or to preserve the amorphicity of the bulk solid and the particles produced from it. Examples of suitable excipients include, but are not limited to, a salt, an ionic compound, a polymer, a cellulose, a sugar, an agar, or a gelatin. More specific examples include, but are not limited to, sodium dodecyl sulfate (SDS), sodium lauryl sulfate (SLS), polyvinypyrrolidone (PVP), polyethylene glycol (PEG), hydroxypropyl methylcellulose (HPMC), polyvinylacetate (PVA), polysorbate, tocopheryl polyethylene glycol succinate (TPGS), a co-polymer comprising any of their monomers and the derivatives or a mixture thereof. The medicinal compounds suitable for use in this invention include an organic material, an inorganic material, or it can be a combination of both so long as the medicinal compound has glass forming ability as the term is known in the art. A material has glass forming ability if it forms a glass when rapidly cooled from a molten liquid state through the glass transition, also known as vitrification. The rapid quenching does not allow for crystallization to occur in the material as it is cooled.

The target holder 5 may be made of an optically durable material such as glass, but this is not necessary as long as the target 4 is held steady in position. The liquid 6 is preferably, de-ionized or distilled water having a resistivity preferably of 1 kOhm cm or greater, but is not so limited. The liquid 6 may also be an ionic solution or a mixture with organic compounds including but not limited to alcohol, ketone, organic acid, aldehyde, aromatic group containing liquids and other volatile organic compounds. Also, the liquid 6 may contain an excipient, a surface stabilizer or co-stabilizers for the produced amorphous medicinal compound particles to maintain their colloidal stability in the liquid or to maintain the amorphicity of the produced particles.

The suitable surface stabilizer and co-stabilizers are preferably a polymer or copolymers. Other suitable surface stabilizers include: surfactants, peptides, proteins and combinations thereof. Representative examples of surface stabilizers and co-stabilizers include, but are not limited to, polymers, copolymers, surfactants, proteins and other pharmaceutical excipients listed in Handbook of Pharmaceutical Excipients, published jointly by the American Pharmaceutical Association and The Pharmaceutical Society of Great Britain (The Pharmaceutical Press, 1986). Examples include: polyvinylpyrrolidones (e.g. PVP K12, PVP K17, and PVP K30); cellulosic polymers, such as HPC-SL, HPC-L, HPMC; copolymers of vinyl pyrrolidone and vinyl acetate (e.g. Plasdone® S630, VA64); poloxamers, such as, Pluronics® F68, F108 which are block copolymers of ethylene oxide and propylene oxide; polyethylene glycols (e.g. PEG 400, PEG 2000, and PEG 4000); polyvinyl alcohol (PVA); tyloxapol; polyoxyethylene Castor oil derivatives; colloidal silicon dioxide; carbomers (e.g. Carbopol 934 from Union Carbide); carboxymethyl cellulose; Na polysorbates such as polysorbate 80, polysorbate 20; benzalkonium chloride; charged phospholipids; sodium docusate; and Aerosol OT (Cytec).

Other examples of surface stabilizers include gelatin, casein, lysozyme, albumin, cholesterol, stearic acid, citric acid, calcium stearate, glycerol monostearate, sodium dodecylsulfate, methylcellulose, non-crystalline cellulose, magnesium aluminium silicate, and Triton® X-200 an alkyl aryl polyether sulfonate available from Rohm and Haas. Mixtures of any the above are also within the scope of invention.

The above excipient, surface stabilizer or co-stabilizers may be added in the liquid 6 either before, during or after laser ablation process. The excipient can also be included in the target 4 during its preparation.

Figure 3:
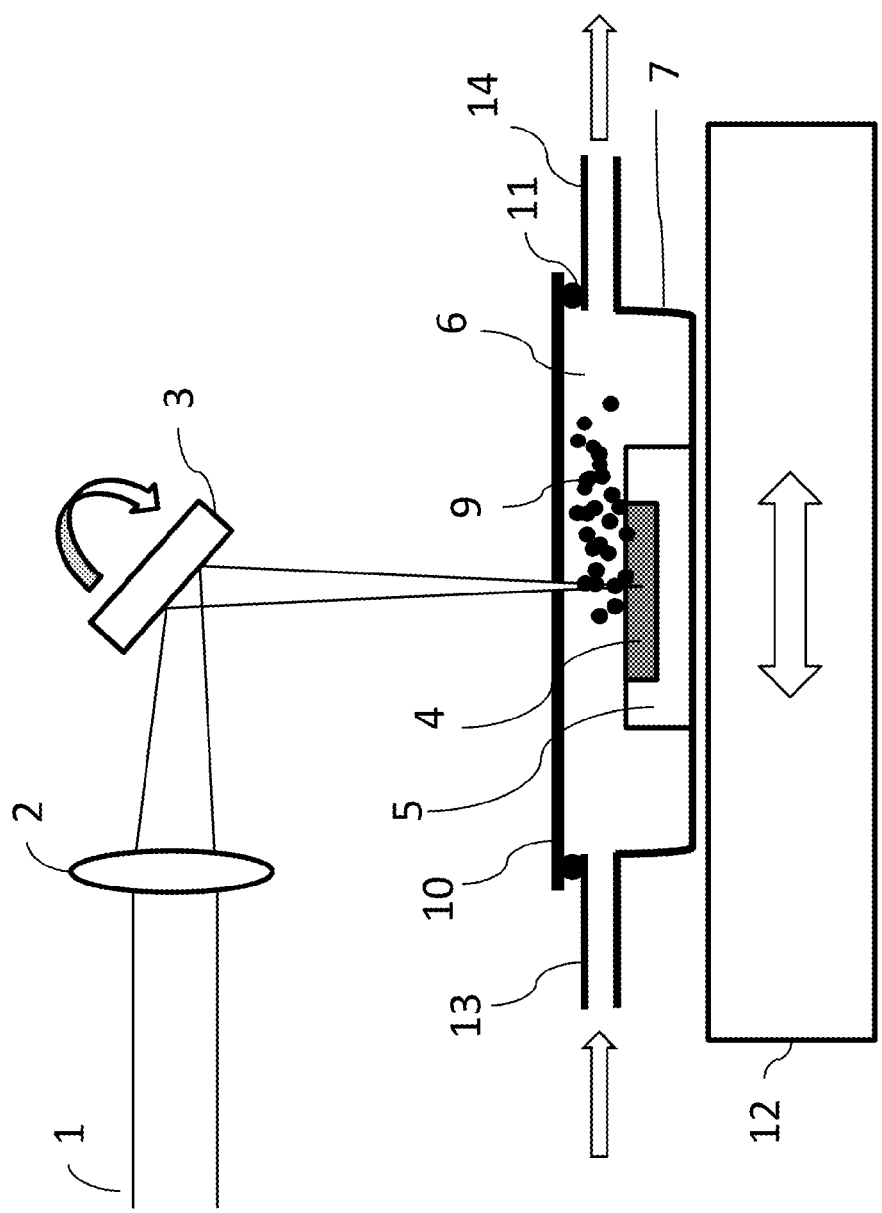
FIG. 3 schematically illustrates a portion of a laser based system for producing amorphous medicinal compound fine particles in a liquid using a circulation system according to the present invention.

In another aspect, a laser based system for producing the amorphous medicinal compound fine particles according to the present invention can also include a liquid circulation system. FIG. 3 schematically illustrates an example of such a laser based system for carrying out the present method. The target 4 is an amorphous solid in a pellet form containing the medicinal compound as described above. The target 4 is submerged several millimeters and preferably less than 1 cm, below the surface of a liquid 6 in a container 7 that is topped by a glass window 10. An O-ring type of seal 11 is placed between the glass window 10 and the container 7 to prevent the liquid 6 from leaking out. The container 7 is fixed on a motion stage 12 that can produce translational motion as indicated of the container 7 and liquid 6. The container 7 has an inlet 13 and an outlet 14 and the liquid 6 flows through the container 7 so that the generated fine medicinal particles 9 can be carried away and collected elsewhere. The flow of liquid 6 should be fast enough to fill the gap between the target 4 and the glass window 10 and to avoid having any gas bubbles generated during laser ablation from staying on the glass window 10.

The flow of the liquid 6 is introduced to the container 7 by a circulation system, not shown, using the inlet 13 and outlet 14. Preferably, the liquid 6 flows at a rate of 1 milliliter per second or greater, and more preferably at a rate of 10 milliliters per second or greater. Liquid flow, beam movement, or both may be used to control heat accumulation in the area of laser irradiation as discussed in U.S. patent application Ser. No. 12/320,617, filed Jan. 30, 2009.

Placing a glass window 10 above the target 4 and filling the gap between the target 4 and the window 10 with flowing liquid 6 is preferred for fine particles generation. Liquid flow can uniformly distribute the generated fine particles 9 in the liquid 6. However, it is to be understood that if there is no glass window 10 on top of the container 7 the upper surface of the flowing liquid 6 can fluctuate during flow and can cause a fluctuation in the thickness of liquid 6 above the target 4. This can change the optical path properties of the laser beam 1 and cause a broader size distribution of the fine particles produced. Therefore, in various preferred embodiments, an optical window 10 above the flowing liquid 6 is introduced to keep a constant depth of liquid 6 above the target 4. When a circulation system is not available, introducing lateral vibration movement, for example perpendicular to the laser beam 1 as indicated in FIG. 3, to the motion stage 12 can also cause liquid 6 flows locally across the ablation spot. The motion stage 12 preferably has a vibration frequency of several Hz and an amplitude of several millimeters. A shaker can also be used to generate liquid circulation, where the circular movement of the shaker can cause circular movement of the liquid 6 too. The glass window 10 might not be necessary in the above situation; however, the use of the motion stage 12 or a shaker will introduce non-uniformity in the thickness of the liquid layer above the target 4 and will cause a broader size distribution of the generated fine particles 9.

Both of the embodiments in FIG. 2 and FIG. 3 show the target 4 was completely submerged in liquid 6, which is not a necessary condition for carrying out the embodiments of the present invention. As long as a portion of the target 4 is in contact with liquid 6, the laser ablation can take place at the target-liquid interface.

For example purposes of illustrating the present invention the poorly water soluble medicinal compound used was curcumin Amorphous curcumin fine particles were produced according to the present invention using an embodiment similar to that shown in FIG. 2. Tumeric is a popular Indian spice with a bright yellow color derived from the rhizomes of *Curcuma longa*, a member of the ginger family (Zingiberaceae). Curcuminoids are the polyphenolic compounds that give turmeric its yellow color and the principal curcuminoid in turmeric is curcumin. Curcumin is water-insoluble and has been used in Asian medicine since the second millennium BC as is mentioned in the Introduction part of "Curcumin: The story so far" by R. A. Sharma et al.: European Journal of Cancer Vol. 41 (2005) 1955. Also, recent research has suggested that curcumin has many active medicinal effects such as: anti-cancer effects; anti-inflammatory effects; anticarcinogenic effects; and hypocholesterolemic effects, see "Theoretical study on Curcumin: A comparison of calculated spectroscopic properties with NMR, UV-vis and IR experimental data" by R. Benassi et al.: Journal of Molecular Structure, 892 (2008) 168. Other proposed effects include: anti-microbial effects; anti-viral effects; antioxidant effects, see "Curcumin Binding to DNA and RNA" by S, Nafisi et al.: DNA AND CELL BIOLOGY Vol. 28 No. 4 (2009) 201; hepato-protective effects; nephro-protective effects; thrombosis suppression; myocardial infarction protective; hypoglycemic; anti-rheumatic, see "Bioavailability of Curcumin: Problems and Promises" by P. Anand et al.: Molecular pharmaceutics, Vol. 4, No. 6 (2007) 807; and protective against Alzheimer's disease, see "Current Treatments for Patients With Alzheimer Disease" by G. G. Osborn et al.: The Journal of the American Osteopathic Association, Sep. 1, 2010 Vol. 110 no. 9 suppl. 8 S16-S26.

Figure 4:
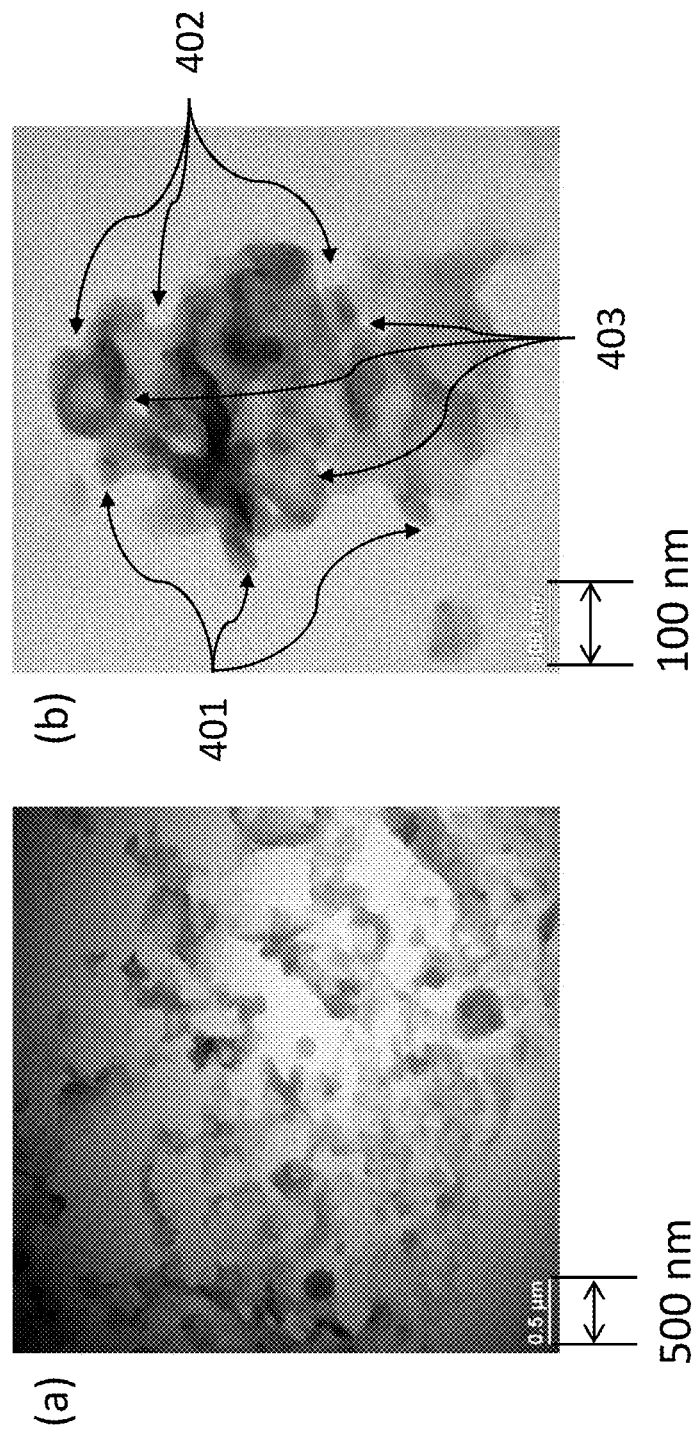
FIGS. 4 (a) and (b) show transmission electron microscope (TEM) micrographs of amorphous fine particles of the medicinal compound curcumin pulverized by a near-Infra-Red femtosecond (fs) pulsed laser according to the present invention.

FIGS. 4 (a) and 4 (b) show the TEM micrographs of amorphous curcumin ultrafine particles produced according to the present invention. The amorphous curcumin ultrafine particle suspension was prepared by laser ablation of an amorphous curcumin target, prepared as described below, in a liquid of de-ionized water. A sample of the suspension was dried on a TEM grid and photographed. A commercially available ultrafast fiber laser, D-1000, from IMRA America was utilized as the pulsed laser source, operating at a pulse repetition rate of 100 kHz, in a process according to the present invention. The laser produces pulses with available energy up to about 10 microJoules and a pulse duration shorter than 700 femtoseconds. The ultrafine particles shown in FIGS. 4(a) and 4(b) were obtained with a lower pulse energy of approximately 3 microJoules. The center of the wavelength of the laser source was about 1045 nanometers. The pulsed laser beams were guided into a two dimensional laser scanner equipped with an f-theta lens having a 10 centimeter focal length.

Figure 5:
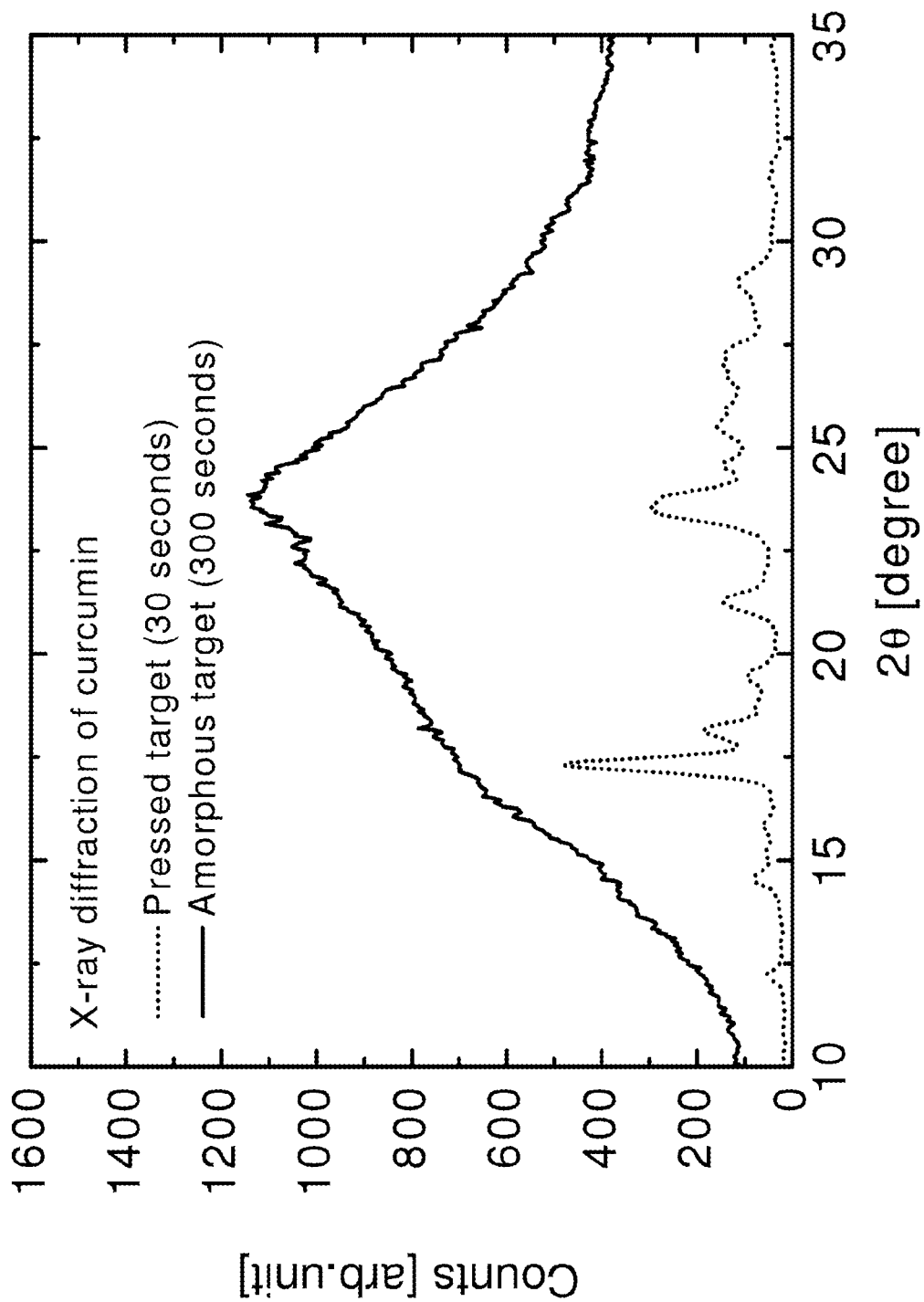
FIG. 5 shows the x-ray diffraction patterns of curcumin targets from a crystalline hydraulically-pressed target, dotted line, and an amorphous target prepared according to the present invention, solid line.

The amorphous curcumin target used in the laser ablation was prepared by heating a crystalline curcumin powder purchased from SIGMA-ALDRICH in a glass dish on a hotplate up to about 210° C. and then rapidly cooling it to room temperature. At 210° C., the crystalline curcumin powder turned into a liquid phase since the melting point of curcumin is 183° C. After the crystalline curcumin powder turned into a liquid phase, the glass dish was immediately moved off of the hotplate and was placed onto a metal plate at room temperature. The quenching rate of the liquid curcumin on the metal plate is faster than 20° C. per minute. FIG. 5 shows the x-ray diffraction profile of the amorphous curcumin target prepared as described above and the x-ray diffraction profile of a target made from a hydraulically-pressed crystalline curcumin powder. The amorphous target profile is shown in the solid line while the hydraulically-pressed crystalline curcumin profile is shown in the dotted line. Even though the accumulation time for the pressed crystalline target was ten times shorter than that for the amorphous target, the sharp Bragg peaks are clearly observed in the pattern of the crystalline sample. On the other hand, the amorphous target shows a broad peak without the Bragg peaks, this lack of Bragg peaks is due to the glassy structure of the amorphous curcumin. In this embodiment, a glassy state of the target was achieved by heating the crystalline powder past the melting point and converting it to a liquid followed by a rapid quenching from the liquid phase. However, there are other ways to make an amorphous bulk target of a medicinal compound from a crystalline starting material such as discussed above, for example with the preferred melt-extrusion process. Also, other thermodynamic parameters such as pressure can be changed to induce a phase transition through which a glassy non-crystalline structure is formed from the bulk crystalline material.

The diameters of the particles shown in FIGS. 4(a) and 4(b) are in the range from sub 100 nanometers to micrometers and they have a complex nano-structure comprising bumps, dents and pores of sub 100 nanometer size, which is beneficial to enlarge the total practical surface area of the particles. Examples of these nano-structures are pointed out by arrows in FIG. 4(b). The set of arrows 401, 402 and 403 indicate nano-sized bumps, nano-sized dents and nano-sized pores, respectively. These irregular geometric shapes are beneficial for increasing the surface area of the nanostructure, and are a characteristic of particles produced by laser ablation. Analysis of the TEM micrographs of dried laser ablation produced particles can be used to characterize the particles quantitatively. In such analysis the laser ablation produced colloidal suspension is initially diluted to reduce particle density and then a sample of the suspension is applied to a TEM grid and dried on the TEM grid. The purpose of dilution is to produce a sample wherein the particles are separated from each other on the grid. Then photographs are taken of the dispersed particles for morphological analysis. The total number of distinct particles are counted and the number of particles having at least one of the three characteristic nano-structures of a bump, a dent or a sub 100 nanometer pore is also determined. These structures are 200 nanometers in size or smaller. Then the percentage of the total number having at least one of these nano-structures, which are characteristic of particles produced by laser ablation, can be determined. Preferably at least 50% of the particles have one or more of the nano-structures, more preferably at least 70% of the particles have one or more of the nano-structures.

Figure 6:
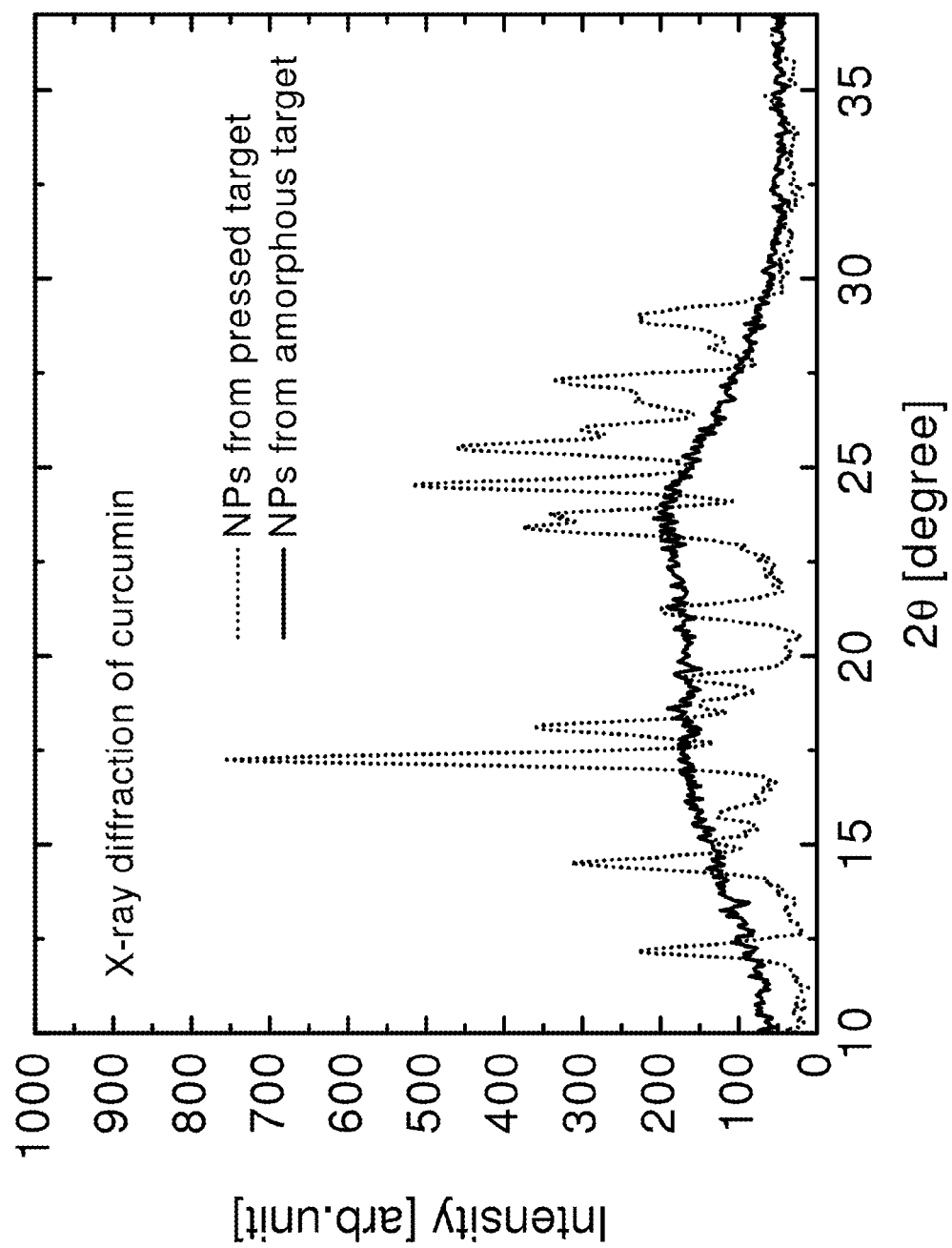
FIG. 6 shows the x-ray diffraction patterns of laser-pulverized curcumin fine particles from either a pressed crystalline target, dotted line, or an amorphous target prepared according to the present invention, solid line.

FIG. 6 shows the x-ray diffraction pattern of amorphous curcumin fine particles produced according to the invention from an amorphous target material compared with crystalline curcumin fine particles which were produced by the laser ablation process using a target made of a hydraulically-pressed crystalline powder. The x-ray diffraction patterns were measured for a few milligrams of the dried fine particles from the respective suspensions using a D8 DISCOVER from Bruker. As is easily seen, the Bragg peaks are absent in the x-ray diffraction profile, shown in the solid line, for the amorphous fine particles produced from an amorphous target while the Bragg peaks appear in the profile, shown in the dotted line, for the fine particles produced from the pressed crystalline target although the intensity level around 35 degree where no prominent Bragg peak is present is similar for these two samples. This indicates that the curcumin fine particles generated from the amorphous target retain the glassy structure of the amorphous curcumin bulk target.

In FIG. 6, the Bragg peaks are absent in the amorphous curcumin fine particles, which means the degree of amorphicity is almost 100%. However, it is to be understood that the present invention doesn't exclude the possibility of a partially amorphous structure of the produced particles. Preferably, the degree of amorphicity of the bulk target and the produced amorphous medicinal compound fine particles according to the present invention is 50% or higher, more preferably 70% or higher, most preferably 90% or higher. A degree of amorphicity can be defined, for example, by scaling the ratio between the height of a certain peak and the background level where no peak is supposed to appear. By way of example, a stepwise procedure for quantifying amorphicity of a sample is as follows: 1. prepare a similar amount of a crystalline solid and an amorphous solid of a medicinal compound; 2. measure the x-ray diffraction for both solids under reasonably similar conditions; 3. choose a representative Bragg peak in the x-ray diffraction pattern of the crystalline solid; 4. find a background level where no peak appears in the x-ray diffraction pattern of the crystalline solid; 5. calculate the ratio between the height of the representative Bragg peak and the background level for the crystalline solid; 6. calculate the ratio of the same signals at the corresponding angles in the amorphous solid; 7. calculate the ratio for the produced particle in the same way; 8. calculate the degree of amorphicity for the produced particle based on the ratio obtained in step 7) by linearly interpolating between the two points obtained in the steps 5) and 6), assuming the crystalline solid and the amorphous solid have 0% and 100% degree of amorphicity, respectively.

Figure 7:
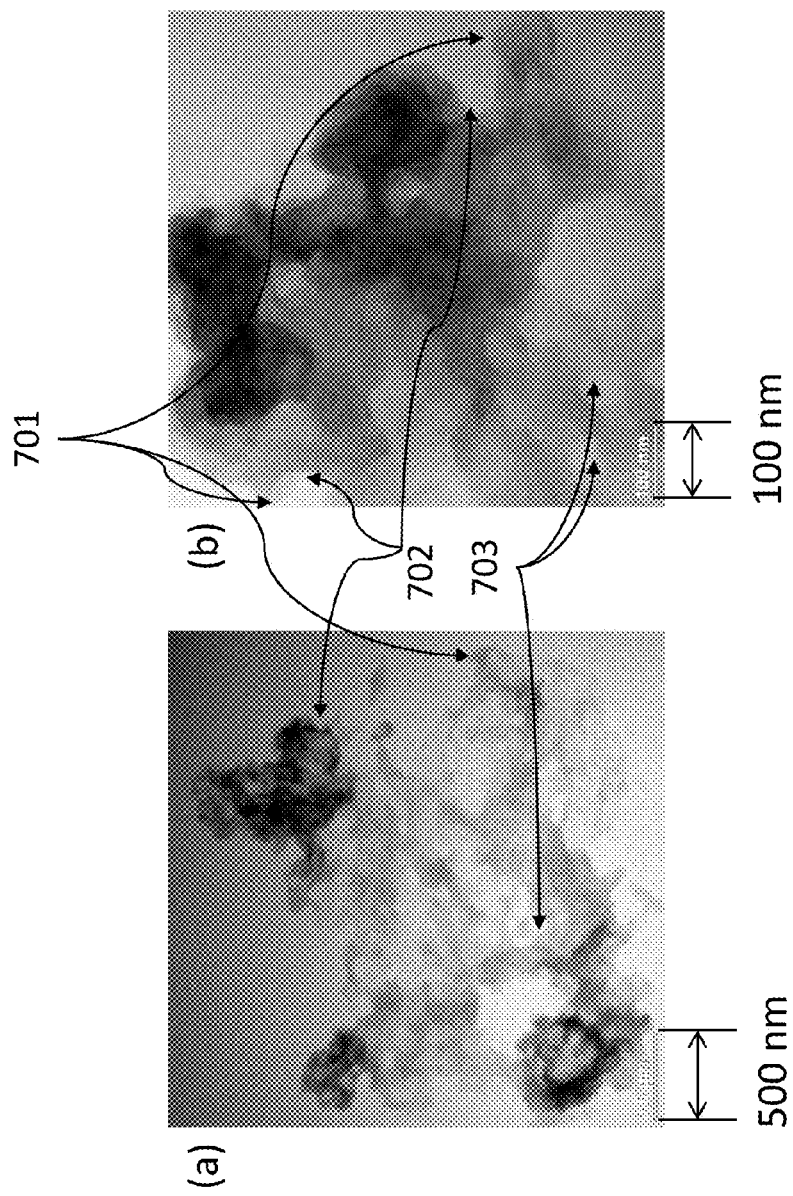
FIGS. 7(a) and (b) show TEM micrographs of amorphous curcumin fine particles pulverized by an UltraViolet nanosecond (ns) pulsed laser according to the present invention.

The laser ablation process may be carried out with various laser systems. As a laser source for the laser beam 1, an ultraviolet pulsed laser having a pulse duration of several nanoseconds can be used as well as the other systems described above. FIGS. 7(a) and 7(b) show the TEM micrographs of the amorphous curcumin ultrafine particles produced using a commercially available ultraviolet nanosecond pulsed laser, Baltic, from EKSPLA. The laser parameters were a pulse energy of 3 microJoule (μJ) with a pulse duration shorter than 30 nanoseconds irradiating the amorphous target at repetition rate of 100 kHz. The laser fluence was adjusted to 3 J/cm$^2$, which was identical to the fluence used above with the near-IR ultrafast laser ablation. The center of the wavelength was 355 nanometers. The laser beam was guided into a two dimensional laser scanner equipped with an UV f-theta lens having about a 16 cm-focal length.

The particles produced by the ultraviolet nanosecond laser are shown in FIGS. 7(a) and 7(b). Similarly to the particles produced using a near-IR ultrashort laser as described above, the particle size is in the range from sub 100 nanometers to micrometers and the particles have an ultrafine structure comprising bumps, dents and pores in the sub 100 nanometers size range. Examples of these nano-structures are pointed out by arrows in FIGS. 7(a) and 7(b). The set of arrows 701, 702 and 703 indicate nano-sized bumps, nano-sized dents and nano-sized pores, respectively. Although the x-ray diffraction pattern is not shown for this sample, it is believed that the amorphous structure of the bulk material is preserved in the fine particles. This belief is supported by the x-ray diffraction data in "Nanonization of megestrol acetate by laser fragmentation in aqueous miliu" by J. P. Sylvestre et al. in Journal of Controlled Release Vol. 149, 273 (2011) wherein it is shown that almost identical spectrum are obtained by in-liquid laser fragmentation regardless of the duration of the laser sources used.

Figure 8:
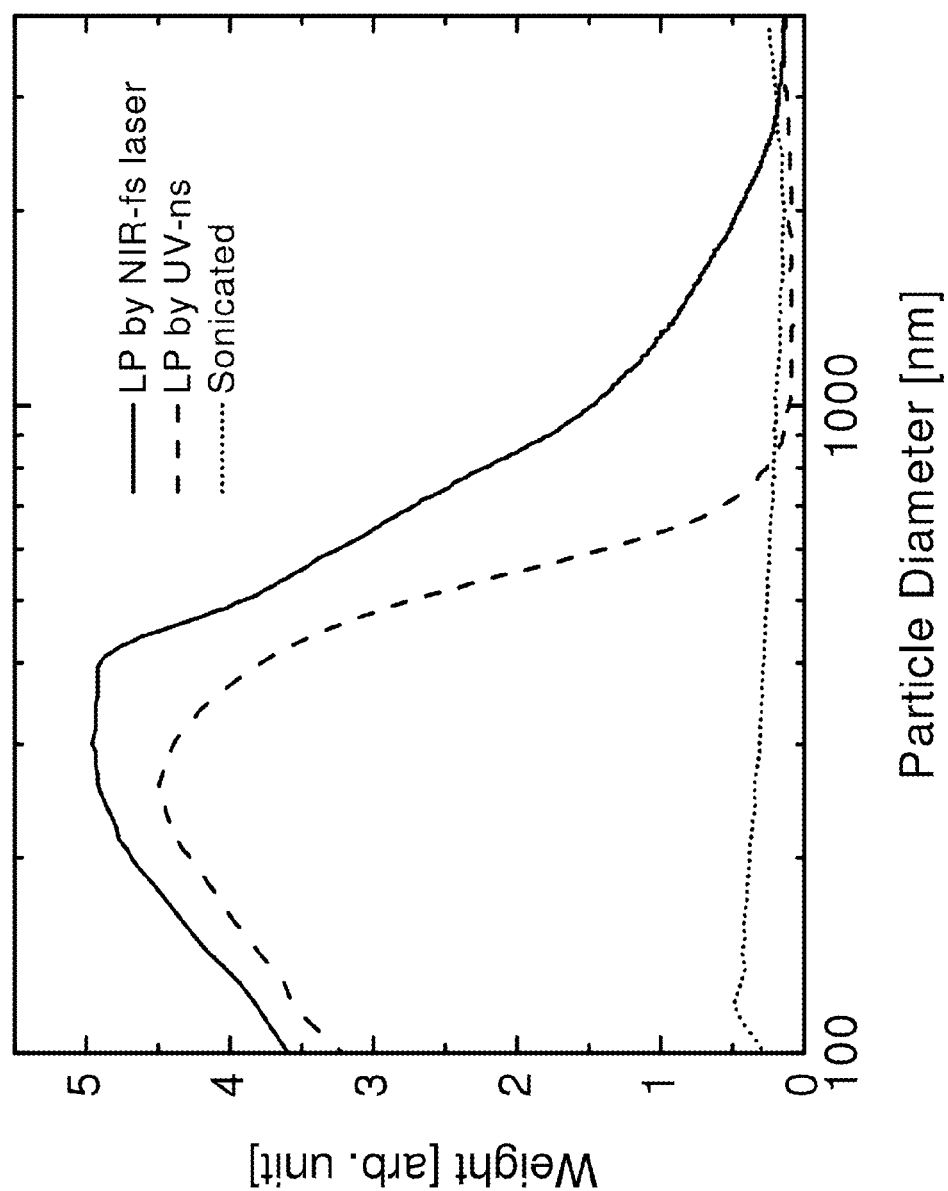
FIG. 8 shows the amorphous curcumin fine particle size distributions prepared by near-IR-fs pulsed laser ablation according to the present invention, UV-ns pulsed laser ablation according to the present invention or by sonication of a curcumin powder suspension.

Regarding the size distribution of the produced amorphous fine particles, in some embodiments use of an ultraviolet nanosecond laser may have the advantage of making the average particle size smaller. FIG. 8 is a comparison of the size distribution of the particle diameters produced by using either a near-IR femtosecond laser or an ultraviolet nanosecond laser on the same amorphous curcumin target according to the present invention. For this size measurement a, CPS Disk Centrifuge DC24000 UHR from CPS Instruments, Inc. was utilized assuming the Particle Nonsphericity parameter as 3, which is the highest for a practical non-spherical particle.

Compared with the particle size suspension made by simple sonication of the curcumin powder in water, both laser ablation processes definitely increased the population of particles smaller than 3000 nanometers. However, in the suspension made using the ultraviolet nanosecond laser according to the present invention, the population of particles is limited to smaller than 1000 nanometers. A possible reason could be that not only is the laser ablation process occurring on the target surface but also laser fragmentation of the generated and suspended particles simultaneously occurs because of the linear absorption of curcumin at 355 nanometers wavelength, which is the center of the wavelength of this laser system.

Figure 9:
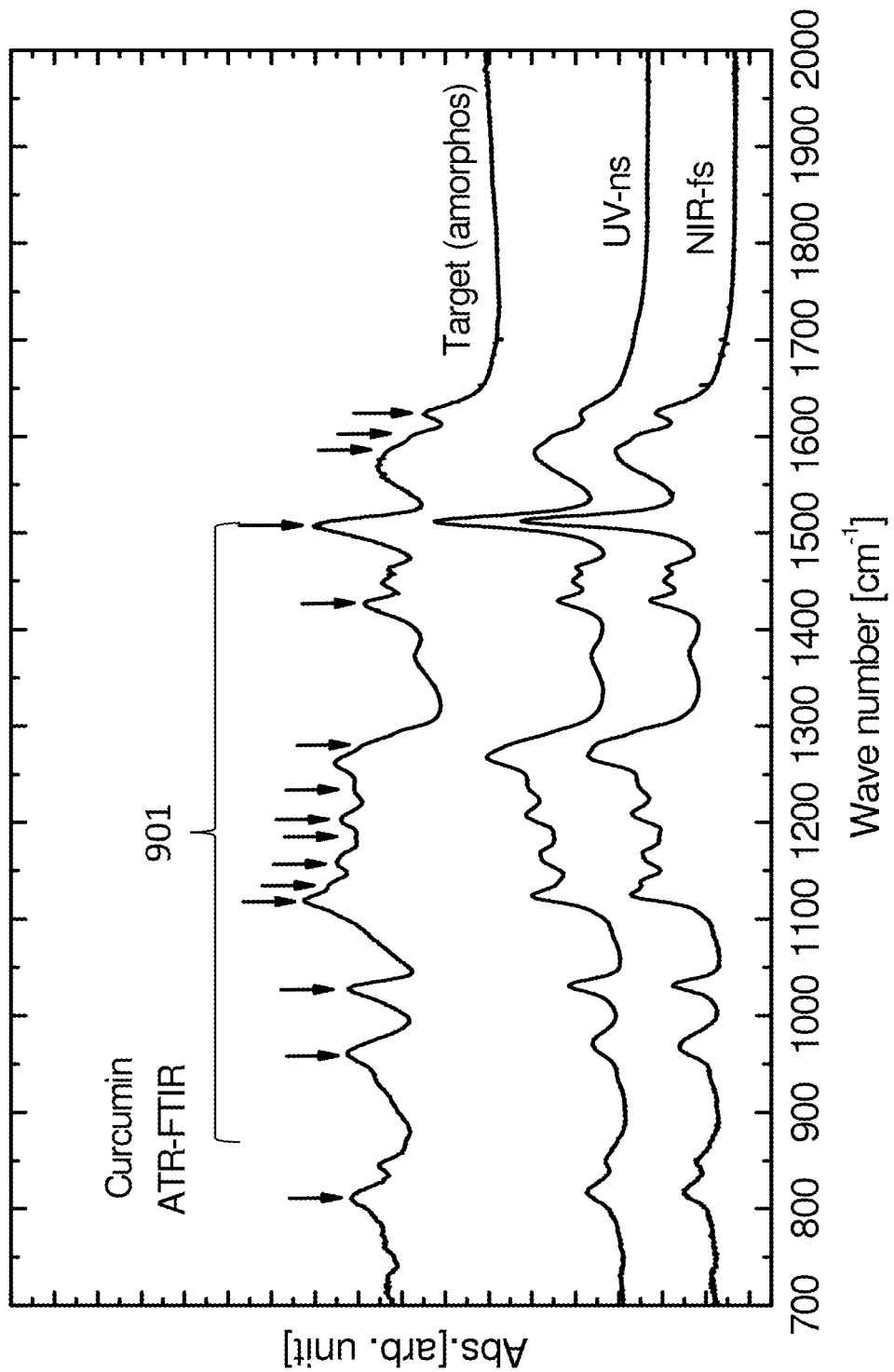
FIG. 9 shows an Attenuated Total Reflectance Fourier Transform InfraRed (ATR-FTIR) spectrum of an amorphous curcumin bulk target material, curcumin fine particles prepared using near-IR-fs pulsed laser ablation according to the present invention, and curcumin fine particles prepared using UV-nanosecond (ns) pulsed laser ablation according to the present invention.

In addition, the almost identical ATR-FTIR spectra in FIG. 9 indicate that the molecular structure of the target material is preserved through the laser ablation process in the produced fine particles regardless of the laser source used. In FIG. 9, the sets of arrows 901 indicate the typical curcumin vibrational lines assigned by R. Benassi et al., see "Theoretical study on Curcumin: A comparison of calculated spectroscopic properties with NMR, UV-vis and IR experimental data" by R. Benassi et al.: Journal of Molecular Structure, 892 (2008) 168.

As discussed above, fine nanoparticles were produced with both near IR ultrashort pulses and UV nanosecond pulses. In various arrangements short wavelength ultrashort pulses may be utilized. Such laser systems may, for example, frequency convert IR pulses to generate visible (e.g. green) or UV pulses, with UV pulses most preferably in the near UV range so as to increase the available peak power.

As yet another alternative, the assignee of the present invention also has developed an ultrashort laser method and system to generate temporally grouped pulses comprising at least two pulses having a temporal separation of shorter than one-third of the inverse of the repetition frequency. This system is called a burst-mode femtosecond pulsed laser which is beneficial to control the size of the generated medicinal fine particles. See M. Murakami, B. Liu, Z. Hu, Z. Liu, Y. Uehara and Y. Che, "Burst-Mode Femtosecond Pulsed Laser Deposition for Control of Thin Film Morphology and Material Ablation", Applied Physics Express, Vol. 2, 042501 (2009) and U.S. patent application Ser. No. 12/401,967, filed Mar. 11, 2009, which is hereby incorporated by reference in its entirety.

In various embodiments of the present invention, stable pure colloids of the amorphous medicinal compound fine particles may be produced. These colloids can be stable at room temperature, 25° C., for at least one week with no added stabilizing agents. However, various embodiments of the present invention do not require that the liquid 6 be free from stabilizing agents. A stabilizing agent can be useful in obtaining a well-dispersed solution.

The colloidal suspension of amorphous medicinal compound fine particles according to the present invention can be used for oral doses, injection or eye-drops. The suspension can be also used as a precursor for further drug formulation. However, a colloidal form may not be necessary. The fine particles can be removed from the suspension by a process including but not limited to evaporation of the suspension liquid by heating, lyophilization, vacuum drying or centrifuging the particles out of solution. Removing the fine particles from the suspension liquid is advantageous to prevent the amorphous medicinal compound fine particles in an amorphous phase from turning into a crystalline phase due to a recrystallization process in the suspension liquid.

At least one embodiment of the present invention is a solution of fine particles of a poorly water soluble medicinal compound comprising: a liquid; and a plurality of fine particles of a medicinal compound dispersed in the liquid. The particles comprise an amorphous solid and have an average particle diameter of from 1 to 5000 nanometers. The fine particles are derived from a poorly water soluble bulk material of the medicinal compound by pulsed-laser-ablation processing of the bulk material and the fine particles retain the chemical composition of the bulk material.

At least one embodiment includes fine particles of an amorphous solid medicinal compound wherein the particles have an average particle diameter of from 1 to 5000 nanometer. The fine particles are derived from a poorly water soluble bulk material of the medicinal compound by pulsed-laser-ablation processing of the bulk material in a liquid and the fine particles retain the chemical composition of the bulk material.

At least one embodiment includes a method of fabricating a solution of fine particles of a medicinal compound. The method includes the steps of: providing a poorly water soluble bulk target material of a medicinal compound comprising an amorphous solid with at least a portion of the target material being in contact with at least a portion of a liquid; and irradiating the target material with a pulsed-laser-ablation beam and forming a plurality of fine particles of the amorphous medicinal compound, wherein the particles have an average diameter of from 1 to 5000 nanometers and wherein the fine particles retain the chemical composition of the bulk target material.

In one or more embodiments the bulk target material comprises an amorphous solid of the medicinal compound.

In one or more embodiments, the particles have an amorphicity of at least 50%, more preferably at least 70%, and most preferably at least 90%.

In one or more embodiments ultrafine particles may have an average particle diameter of from about 1-1000 nm, or from about 1-200 nm.

In one or more embodiments 50% or more of the fine particles have 200 nanometer or smaller ultrafine nanostructures comprising bumps, dents or pores.

In one or more embodiments the fine particles of amorphous solid medicinal compound is active in at least one medicinal effect of: anti-cancer, anti-inflammatory, anti-carcinogenic, hypocholesterolemic, anti-microbial, anti-viral, antioxidant, hepato-protective, nephro-protective, thrombosis suppressing, myocardial infarction protective, hypoglycemic, anti-rheumatic, and protective against Alzheimer's disease.

In one or more embodiments a bulk material of an amorphous solid of the medicinal compound is prepared via a process which includes at least one physical treatment, wherein an initial crystalline structure of the medicinal compound undergoes at least one phase transition thereby converting it into an amorphous solid.

In one or more embodiments solidification of an amorphous solid bulk target material from micron to millimeter sized powder of the medicinal compound occurs by at least one of pressing, melting, or mixing with at least one binder material to form the bulk target material.

In one or more embodiments laser parameters may include: a pulse repetition rate from about 10 kHz to 100 MHz, or from about 10 kHz to 1 MHz; a pulse energy from about 10 nanoJoules to 2 milliJoules, more preferably from 50 nanoJoules to 300 microJoules, or most preferably from about 0.1 microJoules to 100 microJoules; an UV, visible, or near IR wavelength; a pulse duration from about 10 femtosecond to 100 nanosecond, more preferably about 10 femtoseconds to 10 nanoseconds, or most preferably about 30 femtosecond to 10 picoseconds.

In one or more embodiments amorphicity is characterized by an x-ray diffraction pattern exhibiting a smooth background having no distinct Braggs peaks representative of a crystalline structure.

In one or more embodiments the fine particles of the amorphous solid medicinal compound are separated from any suspension liquid.

For purposes of summarizing the present invention, certain aspects, advantages and novel features of the present invention are described herein. It is to be understood, however, that not necessarily all such advantages may be achieved in accordance with any particular embodiment. Thus, the present invention may be embodied or carried out in a manner that achieves one or more advantages without necessarily achieving other advantages as may be taught or suggested herein.

Thus, while only certain embodiments have been specifically described herein, it will be apparent that numerous modifications may be made thereto without departing from the spirit and scope of the invention. It is to be understood that the arrangements are not mutually exclusive. Elements may be combined among embodiments in suitable ways to accomplish desired design objectives. Further, acronyms are used merely to enhance the readability of the specification and claims. It should be noted that these acronyms are not intended to lessen the generality of the terms used and they should not be construed to restrict the scope of the claims to the embodiments described therein.

We claim:

1. A composition of fine particles of a poorly water soluble medicinal compound comprising:
   a liquid;
   and a plurality of fine particles of said medicinal compound dispersed in said liquid, said fine particles comprising an amorphous solid, said fine particles having an average particle diameter of from 1 to 5000 nanometers, and at least 50% of said particles having a plurality of nano-structures each having a size of 200 nm or less and selected from the group consisting of a bump, a dent, a pore, and mixtures thereof, wherein said fine particles are produced from a poorly water soluble bulk material of said medicinal compound by pulsed-laser-ablation processing of said bulk material and wherein said fine particles retain the chemical composition of said bulk material, and said fine particles are characterized by an x-ray diffraction pattern exhibiting a smooth background having no Bragg peaks representative of a crystalline structure.

2. The composition of claim 1, wherein said bulk material comprises an amorphous solid of said medicinal compound.

3. The composition of claim 1, wherein said fine particles are super fine particles having an average particle diameter of from 1 to 1000 nanometers.

4. The composition of claim 1, wherein said fine particles are ultrafine particles having an average particle diameter of from 1 to 200 nanometers.

5. The composition of claim 1, wherein said fine particles of a medicinal compound are active in at least one medicinal effect of: anti-cancer, anti-inflammatory, anti-carcinogenic, hypocholesterolemic, anti-microbial, anti-viral, antioxidant, hepato-protective, nephro-protective, thrombosis suppressing, myocardial infarction protective, hypoglycemic, anti-rheumatic, and protective against Alzheimer's disease.

6. The composition of claim 2, wherein said bulk material of an amorphous solid of said medicinal compound is prepared via a process which includes at least one physical treatment wherein an initial crystalline structure of said medicinal compound undergoes at least one phase transition thereby converting it into an amorphous solid.

7. A medicinal compound containing the composition of claim 1.

8. A medicinal compound made from precursors wherein at least one of said precursors comprises the composition of claim 1.

9. Fine particles of a medicinal compound comprising:
a plurality of fine particles of said amorphous solid medicinal compound, said fine particles having an average particle diameter of from 1 to 5000 nanometers, and at least 50% of said particles having a plurality of nano-structures each having a size of 200 nm or less and selected from the group consisting of a bump, a dent, a pore, and mixtures thereof, wherein said fine particles are produced from a poorly water soluble bulk material of said medicinal compound by pulsed-laser-ablation processing of said bulk material in a liquid, and wherein said fine particles retain the chemical composition of said bulk material, and said fine particles are characterized by an x-ray diffraction pattern exhibiting a smooth background having no Bragg peaks representative of a crystalline structure.

10. The fine particles of claim 9, wherein said bulk material comprises an amorphous solid of said medicinal compound.

11. The fine particles of claim 9, wherein said fine particles are super fine particles having an average particle diameter of from 1 to 1000 nanometers.

12. The fine particles of claim 9, wherein said fine particles are ultrafine particles having an average particle diameter of from 1 to 200 nanometers.

13. The fine particles of claim 9, wherein said fine particles of a medicinal compound are active in at least one medicinal effect of: anti-cancer, anti-inflammatory, anticarcinogenic, hypocholesterolemic, anti-microbial, anti-viral, antioxidant, hepato-protective, nephro-protective, thrombosis suppressing, myocardial infarction protective, hypoglycemic, anti-rheumatic, and protective against Alzheimer's disease.

14. The fine particles of claim 11, wherein said bulk material of an amorphous solid of said medicinal compound is prepared via a process which includes at least one physical treatment wherein an initial crystalline structure of said medicinal compound undergoes at least one phase transition thereby converting it into an amorphous solid.

15. A medicinal compound containing the fine particles of claim 9.

16. A medicinal compound made from precursors wherein at least one of said precursors comprises the fine particles of claim 9.

17. A method of fabricating a solution of fine particles of a medicinal compound comprising the steps of:
a) providing a poorly water soluble bulk target material of said medicinal compound comprising an amorphous solid with at least a portion of said target material being in contact with at least a portion of a liquid; and
b) irradiating said target material with a pulsed-laser-ablation beam and forming a plurality of fine particles of said amorphous medicinal compound, said fine particles having an average particle diameter of from 1 to 5000 nanometers, and at least 50% of said particles having a plurality of nano-structures each having a size of 200 nm or less and selected from the group consisting of a bump, a dent, a pore, and mixtures thereof, wherein said fine particles retain the chemical composition of said bulk target material, and said fine particles are characterized by an x-ray diffraction pattern exhibiting a smooth background having no Bragg peaks representative of a crystalline structure.

18. The method of claim 17, wherein said provided bulk target in step a) has a degree of amorphicity of at least 50%.

19. The method of claim 17, wherein step a) comprises providing a bulk target material prepared via a process which includes at least one physical treatment wherein an initial crystalline structure of said medicinal compound undergoes at least one phase transition thereby converting it to an amorphous solid.

20. The method of claim 17, wherein step a) further comprises forming said bulk target material from micron to millimeter sized powder of said medicinal compound by at least one of pressing, melting, or mixing with at least one binder material thereby forming the bulk target material.

21. The method of claim 17, wherein step b) comprises forming super fine particles having an average particle diameter of from 1 to 1000 nanometers.

22. The method of claim 17, wherein step b) comprises forming ultrafine particles having an average particle diameter of from 1 to 200 nanometers.

23. The method of claim 17, comprising the further step of separating said plurality of fine particles from said liquid.

* * * * *